United States Patent [19]

Czapor

[11] Patent Number: 5,293,886
[45] Date of Patent: Mar. 15, 1994

[54] DENTAL STRIP

[76] Inventor: Henry Czapor, 11501 W. Pleasant Valley, Parma, Ohio 44130

[21] Appl. No.: 19,451

[22] Filed: Feb. 18, 1993

[51] Int. Cl.$^5$ ............................................. A61C 15/00
[52] U.S. Cl. .................................................. 132/329
[58] Field of Search ................ 433/142, 216; 132/321, 132/323, 329

[56]  References Cited
U.S. PATENT DOCUMENTS

| 185,666 | 12/1876 | Brown | 132/321 |
|---|---|---|---|
| 2,772,478 | 12/1956 | Halford | 132/321 X |
| 2,896,639 | 7/1959 | Fleming | 132/321 |
| 3,247,857 | 4/1966 | Kanbar | 132/329 |
| 3,860,013 | 1/1975 | Czapor | 132/323 |
| 3,897,795 | 8/1975 | Engel | 132/321 |
| 3,943,949 | 3/1976 | Ashton et al. | 132/321 |
| 4,237,911 | 12/1980 | White | 132/329 |
| 4,776,358 | 10/1988 | Lorch | 433/216 X |

FOREIGN PATENT DOCUMENTS 1509065  9/1989  U.S.S.R. .............................. 132/321

Primary Examiner—Gene Mancene
Assistant Examiner—Nicholas D. Lucchesi
Attorney, Agent, or Firm—Michael I. Kroll

[57]  ABSTRACT

An improved dental strip which includes a dental rubber tube with a reduced silicon coating and wherein the talcum powder generally used between the inner surfaces of the rubber tube is replaced with by a flavoring compound, which is preferably in the form of a tooth powder, such as baking soda. Many flavoring compounds may be used, such as those which impart a fresh mint taste plus a medicament (e.g., fluoride), which is effective to inhibit the formation of dental caries. Baking soda, as eluded to above will neutralize the odor. A further improvement, and alternative embodiment of the present invention involves improving the appearance of the dental strip and making it easier to remove from a conventional dental strip pack.

10 Claims, 1 Drawing Sheet

DENTAL STRIP

BACKGROUND OF THE INVENTION

1. Field of the Invention

The present invention relates, generally, to an improved dental strip is used to clean food particles from between one's teeth. More particularly, the present invention relates to an improved dental strip wherein the rubber floss utilized to make the dental strip is impregnated with a fluoride medicament and dentifrice. By the addition of flavoring to the dental strip, it can be expected that consumer acceptance of the improved dental strip of the present invention and, thus, the encouragement of routine flossing to aid therapeutic results will be improved.

Additionally, the inversion of the rubber floss strip, or tube, during manufacture of the same, improves utilization of the strip by providing the dental strip with a more rounded shape a conventional tube.

2. Description of the Prior Art

Heretofore, dental strips have been manufactured by die cutting a latex rubber tube. In the manufacturing of such tubes, a silicon coating is applied to the outer surface in order to prevent the same from becoming tacky. The inner surface of the conventional dental tube, or strip, is coated with talcum powder in order to prevent the dental tube from sticking together.

The latex rubber with the silicon coating and talcum powder, unfortunately, leaves a foul taste and odor in one's mouth. As a result, notwithstanding the benefits from flossing on a regular basis, users are inclined to avoid flossing as much as might be beneficial.

This type of dental strip is disclosed and claimed in my earlier patent, U.S. Pat. No. 3,860,013, issued Jan. 14th, 1975.

As will be explained in greater detail hereinafter, the present invention overcomes the prior art deficiencies encountered when the tube of the dental strip becomes stuck together. Additionally, the present invention avoids the deficiencies encountered when users of the dental strips, presently known to the art, seek to avoid proper and regular usage of such strips due to the foul taste and odor.

Finally, the present invention seeks to overcome the deficiencies inherent in the prior art in a manner which is economically competitive for conventional dental strips.

SUMMARY OF THE INVENTION

It is, therefore, an object of the present invention to provide an improved dental strip which will fulfill the needs heretofore recognized and lacking in the prior art.

It is a further object of the present invention to provide an improved dental strip which encourages people to floss regularly.

It is, yet, a further object of the present invention to provide an improved dental strip which has a pleasant flavor and will not leave a foul odor or taste in the mouth of the user.

It is an additional object of the present invention to provide an improved dental strip wherein the inner surfaces of such will have little or no tendency to stick to one another.

It is, still, a further object of the present invention to provide an improved dental strip which may be economically manufactured and offered for sale.

The foregoing and related objects are accomplished by an improved dental strip which includes a dental rubber tube with a reduced silicon coating and wherein the talcum powder generally used between the inner surfaces of the rubber tube is replaced by a flavoring compound, which is preferably in the form of a tooth powder, such as baking soda. Many flavoring compounds may be used, such as those which impart a fresh mint taste plus a medicament (e.g., fluoride), which is effective to inhibit the formation of dental cavities. Baking soda, as alluded to above will neutralize the odor.

A further improvement, and alternative embodiment of the present invention, involves improving the appearance of the dental strip and making it easier to remove from a conventional dental strip pack.

As will be explained in greater detail below, the conventional dental strip, i.e., the dental strip known to the prior art, is a tube with a thin wall and ends which are in elongated form. When the tube is die cut in the manufacturing process, the tube is flattened. This configuration makes removal of a dental strip from the dispenser difficult, as well as not giving the dental strip a good appearance.

In connection with the manufacturing process of the present invention, the dental strip tube is inverted, i.e., turned inside out, after die cutting. This inversion process ensures a more rounded-shape for the dental strip, which allows the dental strip to spring up in an oval shape thereby making it easier to remove the dental strip from the dispenser pack and providing it with a better appearance.

The advantages of the present invention include: a) the improved dental strip is easier to use, since it has a circular handle; b) it is easier to carry since the casing of the dental strip is in a form similar to a matchbook cover; and c) the dental strip of the present invention, in a preferred embodiment, is provided in its dispenser with a removable adhesive backing for easy peel-off.

The improved dental unit of the present invention should preferably be made out of a reasonably soft material so that it will be gentler on the user's gums and, thereby will not cut the gums of the user.

The improved dental strip of the present invention is designed to be easy to use, much like a toothpick might be used between one's teeth. However, the improved dental strip of the present invention is both safer and more efficient than a conventional toothpick.

A further advantage of the present invention is that the rubber latex of the present invention provides an efficient rubber cleaning surface. A slitted band further provides a scrubbing action.

Finally, because of the good flavor embodied by the dental strip of the present invention, persons of all ages, particularly children, will be encouraged to floss on a much more frequent basis. Such increased flossing can be expected significantly reduce tooth decay and gum disease.

It should, of course, be recognized that many modifications to the foregoing are possible and all such modifications should be considered within the scope of the present invention.

To the accomplishment of the above and related objects, the present invention may be embodied in the form illustrated in the accompanying drawing figures, attention being called to the fact, however, that the drawing figures are intended to be illustrative only, and that changes may be made in the specific construction illustrated and described within the scope of the appended claims.

BRIEF DESCRIPTION OF THE DRAWING FIGURES

In the drawing, wherein similar reference numerals denote similar features throughout the several views.

DETAILED DESCRIPTION OF THE PREFERRED EMBODIMENTS

Figure 1:
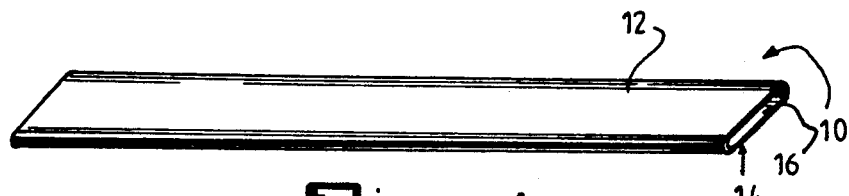
FIG. 1 is a perspective view of a conventional dental strip known to the prior art.

Turning now, in detail, to an analysis of the accompanying drawing figures, FIG. 1 is a perspective view of a conventional dental strip 10 known to the prior art. Such a dental strip is disclosed in U.S. Pat. No. 3,860,013, the pertinent portions of which, such as those relating to the construction of a dental strip per se, are incorporated by reference herein.

Dental strip 10, of the prior art, is produced by die cutting a latex rubber tube 14. In the manufacturing process of such tubes 14, a silicon coating is applied to the outer surface 12 of said tube. This is to prevent the tube from becoming tacky. The inner surface 16 of tube 14 is coated with talcum powder in order to prevent the opposite inner surfaces 16 of rubber tube 14 from sticking to one another. The conventional dental strip 10 of the prior art, unfortunately, suffers from the drawback that the combined rubber with the silicon and talcum powder layers leave a foul taste and odor in the user's mouth.

Figure 2:
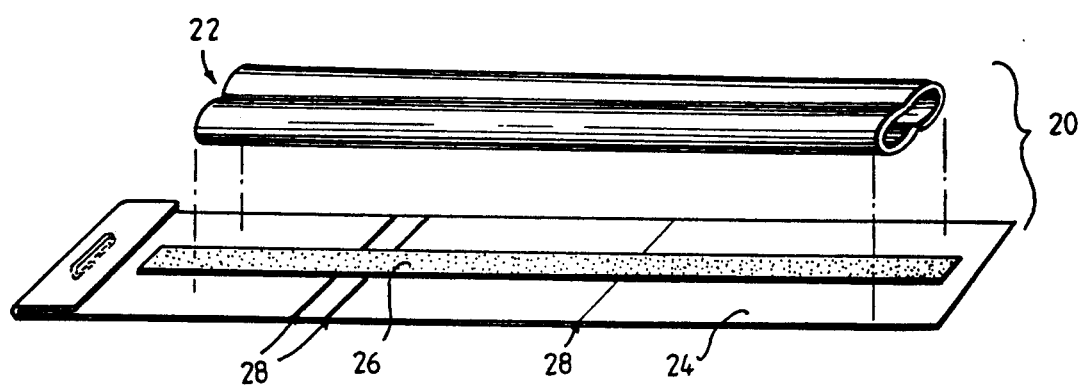
FIG. 2 is a perspective view of the improved dental strip of the present invention, including the preferred dispenser, with adhesive, for containing the dental strip, prior to utilization of the same by a user.

FIG. 2 is a perspective view of the improved dental strip rubber tube 20 of the present invention, including the preferred dispenser 24, with adhesive 26, for containing the dental strip 20, prior to utilization of the same by a user.

In FIG. 2, dental rubber tube 22 is provided with a reduced silicon coating and the talcum powder, which had been provided on the inner surface of such tubing, but is now replaced with a flavoring compound. Many flavoring compounds may be used, such as an added fresh mint taste plus a medicament, preferably containing fluoride. The flavoring compound may be made as part of a conventional tooth powder, which may include baking soda.

The flavoring compound may be applied to the inner surface or outer surface of the tubing of the present invention. However, there is no reason as to why it cannot, on to both the inner and outer surfaces of said tubing.

The use of flavored dental strips as opposed to the unflavored variety provides the user with extraordinary advantages since they will not experience a rubber taste and odor in the mouth. Flavoring is an essential element.

To further improve the dental strips the rubber floss utilized to make the dental strips is impregnated with fluoride medicament and dentifrice.

The present day commercial brands of toothpaste, tooth powder and dental rinse etc. are provided with medicament and flavor that can be used to coat or impregnate the dental strip, encouraging better oral hygiene practices.

All dentifrice consist of sodium, an acid forming ingredient, and starches such as cornstarch and the like. When applied to the dentifrice the starch keeps the sodium in the dentifrice dry and prevents it from reacting (stays dormant) until liquid is added. Liquid saliva in the mouth releases the flavoring to the teeth and mouth. The starch prevents the acid forming ingredients of sodiums from reacting. This also prevents deterioration of the rubber dental strip, providing a longer shelf life.

Flavoring of the dental strip can be achieved by a number of different methods. One or a combination of different dentifrice can be applied to the dental strip with a starch added. One method to impregnate a dentifrice a dental strip is to roll a coat of toothpaste, using a sponge rubber roller, and while the coating is still tacky by means of directed guides, cornstarch is sifted or dusted on the toothpaste, coating the rubber tube. The sifting or dusting is controlled to give the desired flavor concentration. The mixture of toothpaste provides a good adhesion for adequately holding tooth powder and cornstarch mixture by providing a thick coating, achieving a strong noticeable flavor. The tube, after being coated with dentifrice and starch, is inverted, leaving the dentifrice coating in the innermost portion of the tube. This new technique creates a more attractive appearance.

Another method for achieving the flavored dental strip of the present invention, is a mixture of 25% starch and dental rinse (PLAX commercial brand) by weight. The rubber tube is dipped in this solution and dried by means of a microwave oven or tumbled in a heated drum or similar techniques. This process provides a semi-transparent coating of dentifrice to all surfaces of the tube and provides an attractive appearance to the Dental Strip.

There are many different combinations in using the dentifrice for flavoring the dental strip. This determines the process and cost of manufacturing and the quality of the product. The active ingredients, the commercial brands of toothpaste, tooth powder, dental rinse and etc., may be absorbed or coated in any suitable manner with starch or the like. These mixtures may be uniformly applied to the dental strip by rolling, brushing, dipping, dusting, sifting, spraying, or similar techniques or otherwise applied on a rubber material in such a manner as to absorb or coat it thereon. While the foregoing set forth specific features of the invention, modifications may be made without departing from the spirit of the present invention.

The Dispenser is made of cardboard and the inner portion has a double coated glazed finish. This provides a hard surface for die cutting rubber tubes. As stated, the outside portion of the dispenser is the absorbent side (has no coating) this side is treated with pleasant odors, i.e. peppermint. The product is sold in a plastic ziplock bag which holds the scent for a greater length of time, providing a greater attraction to the buyers. The plastic ziplock bag provides the user with a place to store the dispenser during usage of the dental strip, which keeps it fresh and clean for a greater period of time.

Now there is a scent and flavor with the same characteristic (peppermint or the like). The dispenser scent, which gives off a gas, absorbs into the dentifrice (flavor on dental strip) and into the rubber dental strip. The plastic bag enclosure allows the scent of dental strip to be retained.

The customary way of removing food particle lodged between the teeth after a meal is to use a toothpick. The dental strip can be a combination of dental floss and a toothpick, making it more effective in removing food particles. The dental strip can be used for on the spot flossing whenever discomfort occurs. The dental strip can be disguised and is therefore less conspicuous when flossing in public. Changing the color of the dental strip from a bright yellow, for example, to a tan color, allows it to blend in with the color of the human skin and be camouflaged.

The circular band is easy to handle. A small portion of the band is exposed when flossing because the band is stretched, fitting snugly around the fingers. With the new camouflage coloring the dental strip is almost unnoticeable when flossing. Because of the circular band, flossing can be done using one hand. The elastic band measures ¾ of an inch in a flat position, stretches to about four inches when in use, and then returns to its original small shape to facilitate disposal.

Dispenser - The peel off flexible unit is similar to a matchbook and is easy to carry. The Dental Strip is not harsh and will not cut the gums. It is compressible to work in narrow spaces. The Dental Strip makes it easy to form healthy flossing habits, which helps reduce tooth decay and gum disease.

In order to improve the appearance of the rubber tubing 22 of the present invention, as well as to make the same more efficient and easier to remove from the dispenser 24, following a die cutting of the tube, wherein the thin wall and elongated ends are formed, the tube 22 is inverted such that the original outer surface is on the inside and the original inner surface is now on the outside.

This procedure provides the tubing 22 with a more rounded shape, or somewhat oval shape, which makes it easier to remove the dental strip from the dispensing packet.

The dispensing packet 24 is preferably made in a manner which is similar to that of a matchbook cover and which may readily be unfolded as, for example, along creases 28.

Dispensing packet 24 is, further, preferably provided with an adhesive strip from which the rubber tubing 22 may be readily removed therefrom. This adhesive strip is preferably a double-sided adhesive with one side affixed to the dispenser and the opposite side being removably affixed to tubing 22. This embodiment is designed to allow for an easy peel-off of tubing 22 from dispenser 24.

Figure 3:
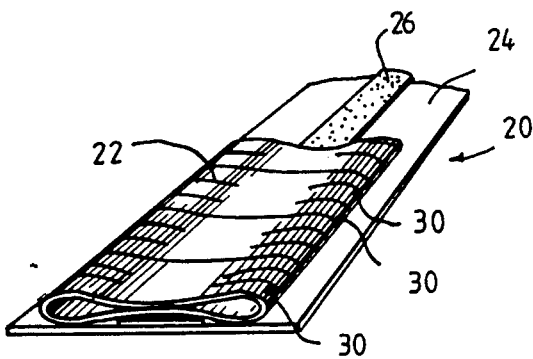
FIG. 3 is a lengthwise perspective view of the improved dental strip of the present invention showing the dental strip tubing, as slitted, and the dispenser with the adhesive backing for the dental strip tubing.

FIG. 3 shows the improved dental strip tubing 22, as slitted at 30, and dispenser 24 with an adhesive backing 26 for dental strip tubing 22.

Figure 4:
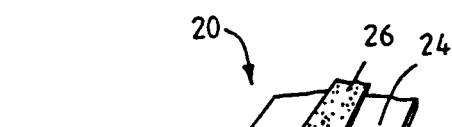
FIG. 4 is a lengthwise perspective view of the improved dental strip of the present invention, as shown in FIG. 3, with the dental strip tubing being shown in an expanded state; and, FIG. 5 is a cross-sectional view, taken along line 5—5 of FIG. 4, and showing the several layers, coatings, adhesive and dispenser comprising the present invention.

FIG. 4 shows the improved dental strip in an expanded state.

Figure 5:
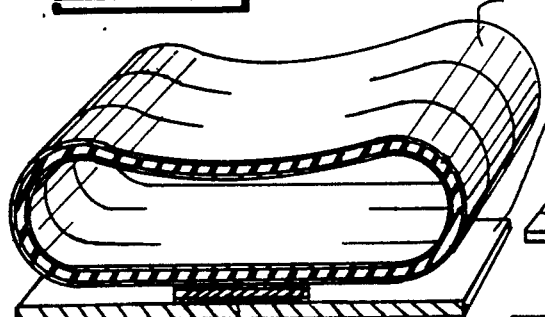

FIG. 5 is a cross-section view, taken from a prospective angle, along line 5—5 line of FIG. 4, said FIG. 5 showing the several layers, coatings, adhesive and dispenser comprising the present invention.

Reference numeral 24, as explained above, represents the dispenser pack. In FIG. 5, the adhesive is shown as tape 26 with double-sided adhesive glue thereon. Reference numeral 22 represents the rubber tubing. This rubber tubing includes a silicon layer thereon and is, thereafter, preferably fully coated with the flavoring compound, as described heretofore.

It will be obvious to those skilled in the art that numerous modifications may be made to the present invention, with all such modifications being intended to be included with the scope of the present invention.

LIST OF REFERENCE NUMERALS 10 conventional dental strip
12 outer surface of conventional dental strip
14 latex rubber tube
16 inner surface of conventional latex rubber tube
20 dental strip of the present invention
22 rubber tube
24 dispenser pack
26 adhesive
28 creases of dispenser pack
30 slits of rubber tube of present invention It will be understood that each of the elements described above, or two or more together, may also find a useful application in other types of methods differing from the type described above.

While certain novel features of the present invention have been shown and described and are pointed out in the annexed claims, the present invention is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will be fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. A dental strip comprising:
    a latex rubber tube having a silicon layer with a flavoring compound atop said silicon layer,
    said latex rubber tube being provided with a series of slits cut circumferentially, wherein
    said flavoring compound is applied on an inner surface and an outer surface of said latex rubber tube.

2. A dental strip in combination with a dispenser pack in the form of a matchbook, wherein said dental strip comprises;
    a die cut latex rubber tube having a silicone layer with a flavoring compound atop said silicone layer to eliminate any rubber taste or odor,
    said latex rubber tube being provided with a series of slits cut circumferentially,
    said flavoring compound being applied on both an inner surface and an outer surface of said latex rubber tube, and wherein
    said dental strip is inverted, i.e. turned inside out, before die cutting so as to ensure a more rounded shape by allowing said dental strip to spring up into an oval shape allowing easier removal from said dispenser pack.

3. The combination of claim 2, wherein said flavoring compound on said latex rubber tube comprises;

a tooth powder including baking soda.

4. The combination of claim 2 wherein said flavoring compound on said latex rubber tube comprises;

fluoride medicament, dentifrice, and flavoring.

5. The combination of claim 2, wherein said flavoring compound on said latex rubber tube comprises;

a tacky layer of flavored toothpaste rolled on to said latex rubber tube with a sponge rubber roller, a mixture of tooth powder and cornstarch dusted upon said toothpaste.

6. The combination of claim 5, wherein said mixture of tooth powder and cornstarch provides a non-tacky coating for said dental strip.

7. The combination of claim 5, wherein said latex rubber tube is turned inside-out after being coated with said flavoring compound so as to position said flavoring compound on the innermost portion of said latex rubber tube and create an attractive external appearance.

8. The combination of claim 2, wherein said flavoring compound on said latex rubber tube comprises;

a dental rinse mixed with starch to form a dipping solution for said latex rubber tube, wherein said latex rubber tube is dipped in said dipping solution and then dried in a microwave oven.

9. The combination of claim 2, wherein said dental strip is colored so as to blend in with the color of the users skin and act as a camouflage.

10. The combination of claim 2, wherein said dental strip is highly elastic to allow stretching for ease of use.

* * * * *